United States Patent
Colin et al.

(10) Patent No.: US 7,993,665 B2
(45) Date of Patent: Aug. 9, 2011

(54) WOUND HEALING AGENT AND COMPOSITION

(75) Inventors: Sylvie Colin, Paris (FR); Salman Al-Mahmood, Paris (FR)

(73) Assignee: Gene Signal International SA, Lausanne (CH)

( * ) Notice: Subject to any disclaimer, the term of this patent is extended or adjusted under 35 U.S.C. 154(b) by 0 days.

(21) Appl. No.: 12/029,036

(22) Filed: Feb. 11, 2008

(65) Prior Publication Data
US 2008/0241210 A1 Oct. 2, 2008

Related U.S. Application Data (62) Division of application No. 11/704,313, filed on Feb. 9, 2007, now abandoned.

(30) Foreign Application Priority Data

Feb. 9, 2007 (EP) .................................. 07290164

(51) Int. Cl.
*A61F 2/00* (2006.01)
*A61L 15/00* (2006.01)
*A61K 38/00* (2006.01)

(52) U.S. Cl. ......... 424/423; 424/447; 514/1.1; 514/13.3

(58) Field of Classification Search .................. None
See application file for complete search history.

(56) References Cited

U.S. PATENT DOCUMENTS

| 4,131,206 A | 12/1978 | Kawads et al. |
| 5,133,511 A | 7/1992 | Mack et al. |
| 6,007,017 A | 12/1999 | Vorwerk |
| 7,553,492 B2 * | 6/2009 | Al-Mahmood et al. ... 424/198.1 |
| 2008/0108551 A1 * | 5/2008 | Horobin et al. ............ 514/2 |

FOREIGN PATENT DOCUMENTS

| WO | WO 03/029271 A2 * | 4/2003 |
| WO | WO 03/074073 | 9/2003 |

OTHER PUBLICATIONS

Li et al. Angiogenesis in Wound Repair: Angiogenic Growth Factors and the Extracellular Matrix. Microscopy Research and Technique 60:107-114 (2003).*

Sato et al., "Autocrine activities of basic fibroblast growth factor: Regulation of endothelial cell movement, plasminogen activator synthesis, and DNA synthesis," *The Journal of Cell Biology*, vol. 107, 1988, pp. 1199-1205.

* cited by examiner

*Primary Examiner* — Marianne P Allen
*Assistant Examiner* — Regina M Deberry
(74) *Attorney, Agent, or Firm* — Young & Thompson (57) ABSTRACT

The present invention relates to a wound-treating agent and to a composition for the treatment of wounds comprising a polypeptide having the amino acid sequence of SEQ ID NO:2, or of a polypeptide having at least 50%, preferably 70%, more preferably 90% identity with the amino acid sequence of SEQ ID NO:2.

9 Claims, 7 Drawing Sheets

SEQUENCE LISTING

```
<160> NUMBER OF SEQ ID NOS: 2

<210> SEQ ID NO 1
<211> LENGTH: 2153
<212> TYPE: DNA
<213> ORGANISM: Homo sapiens

<400> SEQUENCE: 1
caaagagaca aacactgatg aagccgctaa tgacaatatg gcagttcgcc ccaaagagcg        60
cagcagcctg agctctagac agcatccgtt tgtaaggagc agtgtgatag tgcgctcaca       120
gaccttttct ccaggagagc ggaaccagta catctgcagg ttaaatcgga gtgacagtga       180
cagttcaacc ctggctaaaa aatcactgtt tgtgagaaac tccaccgaac gccgcagttt       240
gagggtcaaa aggacggttt gccagtcagt ccttagaaga acaacacagg aatgcccagt       300
gcggacatct ctagacttag aactggacct tcaggcatct ctgacccggc agagccgcct       360
caatgatgag ctgcaggcgc tgagggactt gcggcagaag ctggaggaac tgaaagctca       420
gggagagact gaccttccac caggcgtgct ggaggatgag aggttccaga ggcttctgaa       480
gcaagctgag aagcaggctg aacagtccaa agaagagcag aagcaaggtc tgaatgcaga       540
gaagttgatg aggcaagtct ccaaggacgt gtgtcggctc cgggagcaga gccagaaggt       600
gcctcggcag gtgcagtcct tcaggagaa gattgcctac ttcaccagag caaagataag       660
catcccatcc ctgccagctg atgatgtgtg attacatgac ttaagaaatt atttttttcat      720 ctgttcactt tcttagggag ggtaaaagac tgaagatttg tgttttttgtt ttggtgtttg     780 gttttttttg gtaacgtaac tgtcaactct tgaagaactt ttatttcaca tcagattttc     840
aacacattaa tttgtaaagt accttgagtg taattttttat atgcttaaaa aagaaaaaat     900
catataagaa agatgggata acctggtaca caaatgttgc ccagtatgtg cgcattgcca     960
gtggacttca ttttgtaaaa atggaataga ggcagtaccc caccatgtgt actgttgagc    1020
cggctgttga gaaacaactt ggttcagccg gtggttttgc ttctcctttg tgttcctgtg    1080
agtaggctgt gccgatggca gcagcgccac gtggtatctg tgcgctggcg aggagaggag    1140
cgctttccat ttggaggcag tgtgagcaca cgctggagtg cagcgttcca aagtccgccc    1200
gaaatggatg ctgcgtccac ggccatcacc tgtgcgggaa cacctggttt ccttaagaca    1260
atttcctttt tgtcctttta tattttctcta aagaaaacta agatataaac taccaagtgc    1320
tcttaagaat aaaaataaga ataagaatac aaaggagcac tactcttggc tacacgaaag    1380
```

-continued

```
atcttgggat tcatgacact gagggcaggg agaagaaaga acaccagcca cgcagagata    1440
caaataagct catcaaatga gcagctggtt tgtctcactc agcctgaatt tgcattaagt    1500
gttcaaaagt gagtttctgg cttgcactag tgttttgccc taaatctaag gatggtgcct    1560
agtggtggcc ctgtgttctg aggacagaga gagctggagg ggtggaggga aatgcatcgg    1620
cactcatttg gtgtaaccaa gaagaggggg aaagatgtct tgatagaatc aaagttgcca    1680
aaaacaaaga agagtttatc aagcagattt ctaacattta gtagaaacta cttcatagct    1740 ctcatttta gggggttcta tctataattt atggtaaata gttgggaggc aaagggaaga    1800
atgtgtgtgg gggtattatt aatttgaagt ataagctaaa ttgtttatta aaaagcctat    1860
tttggatgaa caagtttaga gagataaact gactaatgtg tcctccagtt tagaatttca    1920
ccttacccga cccaggcact tcttaaaaac acagatcctc agtgcagctc tgccagcatc    1980
aaggctttta aaatatgtag tatttaggcc atttaaacca tacttattac tcaataaccc    2040
aagaaacaat tttgggttag ccatctaata tagcaaataa aatagatttt ttaaagaaat    2100
ccaaaattgt cttaaaggaa tggacccctt gaagaaaaaa aaaaaaaaaa aaa          2153
```

<210> SEQ ID NO 2
<211> LENGTH: 217
<212> TYPE: PRT
<213> ORGANISM: Homo sapiens

<400> SEQUENCE: 2

```
Met Ala Val Arg Pro Lys Glu Arg Ser Ser Leu Ser Ser Arg Gln His
  1               5                  10                  15

Pro Phe Val Arg Ser Ser Val Ile Val Arg Ser Gln Thr Phe Ser Pro
             20                  25                  30

Gly Glu Arg Asn Gln Tyr Ile Cys Arg Leu Asn Arg Ser Asp Ser Asp
         35                  40                  45

Ser Ser Thr Leu Ala Lys Lys Ser Leu Phe Val Arg Asn Ser Thr Glu
     50                  55                  60

Arg Arg Ser Leu Arg Val Lys Arg Thr Val Cys Gln Ser Val Leu Arg
 65                  70                  75                  80

Arg Thr Thr Gln Glu Cys Pro Val Arg Thr Ser Leu Asp Leu Glu Leu
                 85                  90                  95

Asp Leu Gln Ala Ser Leu Thr Arg Gln Ser Arg Leu Asn Asp Glu Leu
            100                 105                 110

Gln Ala Leu Arg Asp Leu Arg Gln Lys Leu Glu Glu Leu Lys Ala Gln
        115                 120                 125

Gly Glu Thr Asp Leu Pro Pro Gly Val Leu Glu Asp Glu Arg Phe Gln
    130                 135                 140

Arg Leu Leu Lys Gln Ala Glu Lys Gln Ala Glu Gln Ser Lys Glu Glu
145                 150                 155                 160

Gln Lys Gln Gly Leu Asn Ala Glu Lys Leu Met Arg Gln Val Ser Lys
                165                 170                 175

Asp Val Cys Arg Leu Arg Glu Gln Ser Gln Lys Val Pro Arg Gln Val
            180                 185                 190

Gln Ser Phe Arg Glu Lys Ile Ala Tyr Phe Thr Arg Ala Lys Ile Ser
        195                 200                 205

Ile Pro Ser Leu Pro Ala Asp Val
    210                 215
```

WOUND HEALING AGENT AND COMPOSITION

The present invention relates to the healing of wounds. Particularly, the present invention relates to a wound healing agent, compositions containing said wound-healing agent, and medical devices containing the same.

Wound healing in tissues is a complex reparative process. For example, the skin wound healing process involves the recruitment of a variety of specialised cells to the site of the wound, extracellular matrix and basement membrane deposition, angiogenesis, selective protease activity and re-epithelialisation.

There is always a need to provide substances that promote the healing of wounds. It is often desirable to increase the rate of healing in the case of acute wounds and chronic wounds, or for generally healing compromised individuals (for example the elderly). The wounds may severely influence quality of life or even result in death and therefore the rate of healing often needs to be increased as much as is clinically possible.

Number of wound healing agents and compositions already exist on the market, but none are completely satisfying. Though, it is still an important issue to provide alternative wound healing agents and compositions, resulting in effective, rapid and aesthetically acceptable wound repair.

WO 03/074073, in the name of the Applicant, describes a family of 54 genes involved in the regulation of angiogenesis. Amongst these genes, "gene 156" (SEQ ID NO. 1 in this specification), which encodes "protein 156A" (SEQ ID NO. 2 in this specification), and also called Angiodensine in WO 03/074073, has been described as pro-angiogenic. Protein 156A comprises 217 amino-acids, and has a mitochondrial sequence signal, detected by in silico experiments. Protein 156A does not contain any transmenbrane domain nor conserved domain. WO 03/074073 describes that the expression of an antisens of the gene 156, i.e. the inhibition of gene 156, in human endothelial cells inhibits the formation of capillary tubes. WO 03/074073 further foresees a potential pro-angiogenesis activity for gene 156 and protein 156a.

Going deeper in their researches, the inventors surprisingly found that protein 156A showed a strong in vitro and in vivo wound healing activity. WO 03/074073 mentioned only potential in vitro pro-angiogenic activity for protein 156A, and the inventors had thus no idea about the possible behaviour of protein 156a on wound healing in vivo.

The inventors were thus really surprised to note the strong efficiency of protein 156A on wound repair.

In addition, inventors found that protein 156A was also particularly active on the final aesthetic aspect of the scar, which appeared more regular and less colored.

The present invention thus relates, in a first aspect, to a wound-treating agent comprising a polypeptide having the amino acid sequence of SEQ ID NO:2, or of a polypeptide having at least 50%, preferably 70%, more preferably 90% identity with the amino acid sequence of SEQ ID NO:2.

By the term "polypeptide having at least 50%, preferably 70%, more preferably 90% identity with the amino acid sequence of SEQ ID NO:2" it is meant any polypeptide having 50%, preferably 70%, more preferably 90% identity with the amino acid sequence of SEQ ID NO:2 and presenting a wound healing activity. It also includes fragments of protein 156A having a wound healing activity.

The term "wound" as used herein refers to, but is not limited to:
injuries to epidermis and/or dermis of the skin,
wounds resulting from damage, injury or trauma to an internal or external tissue or organ such as for example the eye, mucous, lung, kidney, heart, gut, tendons or liver,
injuries or damages to vascular tissues, such as for example veins, venules, arteries, and capillaries.

In this specification, the term "wound treating" is used to describe all the different steps involved in the healing of wounds. It therefore includes the steps of forming a clot that plugs the defect, invasion of the clot by inflammatory cells and then of fibroblasts and capillaries to form a contractile granulation tissue that draws the wound margins together, and migration forward of the cut epidermal edges to cover the denuded wound surface. The term "Wound treating" is not limited to the healing of the skin, but also includes the tissue repair of other types of wounds, as listed above.

In a second aspect, the present invention also relates to a method of treatment of a wound comprising administering to a subject in need thereof, a therapeutically effective amount of SEQ ID NO:2, or of a polypeptide having at least 50%, preferably 70%, more preferably 90% identity with the amino acid sequence of SEQ ID NO:2.

By the term "therapeutically effective amount" it is meant an amount that allows the achievement of the contemplated medical end, i.e. the healing of a wound, without producing unacceptable toxic symptoms. Said "therapeutically effective amount" will vary with the factors such as the particular condition being treated, the physical condition of the patients and the duration of the treatment.

The present invention further relates, in a third aspect, to a wound-treating composition comprising a polypeptide having the amino acid sequence of SEQ ID NO:2, or of a polypeptide having at least 50%, preferably 70%, more preferably 90% identity with the amino acid sequence of SEQ ID NO:2 in association with any suitable excipient for the treatment of wounds.

In a particular embodiment, the endotoxins are eliminated from the composition containing the polypeptide having the amino acid sequence of SEQ ID NO:2, or of a polypeptide having at least 50%, preferably 70%, more preferably 90% identity with the amino acid sequence of SEQ ID NO:2.

One of the principal advantages of the wound treating agent and of the wound treating composition according to the invention is the increase of the healing rate and the return of the injured tissue histologically very close to the native tissue.

Moreover, inventors pointed out that the wound treating agent and the wound treating composition according to the invention are particularly active on the stimulation of endothelial cell migration in vitro. Protein 156A also seems to play a global role on the healing of wounds, not limited to a single stimulation of angiogenesis but to a wide stimulation of the wound repair process, comprising the regeneration of the cells in the dermis and the epidermis.

The present invention also relates to a wound-treating composition comprising a polypeptide having the amino acid sequence of SEQ ID NO:2, or of a polypeptide having at least 50%, preferably 70%, more preferably 90% identity with the amino acid sequence of SEQ ID NO:2 for use in a method of treatment of wounds of the human or animal body.

In a particular embodiment, the wound-treating compositions as described above, comprise at least two active substances, one of which being a polypeptide having the amino acid sequence of SEQ ID NO:2, or of a polypeptide having at least 50%, preferably 70%, more preferably 90% identity with the amino acid sequence of SEQ ID NO:2. In another embodiment, a further active substance is a haemostatic active substance, a growth factor, an anti-infective substance, an analgesic substance, an anti-inflammatory substance, or a combination thereof.

In still another embodiment, the wound treating composition according to the invention is in a form suitable for topical, systemic, oral, subcutaneous, transderm, intramuscular or intra-peritoneal administration.

A suitable form for topical administration comprise liquid, ointment, cream, gel, hydrogel, cataplasm, pomade, liniment, milk, lotion, emulsion, spray, aerosol, collyrium, drops, powder.

A suitable form for systemic administration comprises injectable solution and suppository.

A suitable form for oral administration comprises drinkable suspension, syrup, tablets, capsules, pill.

According to the invention, in the wound treating composition as described above, said polypeptide is present in an amount from 0.01 to 90% in weight, preferably from 0.1% to 10% in weight, more preferably from 1% to 5% in weight.

In a particular embodiment, the composition oL the invention is in a liquid form, and the active polypeptide is present in an amount from 0.01 mg/mL to 5 mg/mL, preferably from 0.1 mg/mL to 1 mg/mL, more preferably about 0.5 mg/mL.

A "composition" in the sense of the invention encompasses pharmaceutical, including dermatological, compositions and cosmetic compositions.

The term "suitable excipient", include well known raw materials such as animal and plant oils, mineral oils, synthetic oils, ester oils, waxes, linear higher alcohols, fatty acids, surfactants, phospholipids, gelling and/or thickening agents, alcohol, polyols (including glycerine and propylene glycol), fillers such as clay minerals, soft-focus powders, preservatives, fragrances, pigments and purified water. This term also includes polysaccharides, such as for example mannans, gluco mannans, galactomannans, fucomannans, proteoglycans, glucosaminoglycans, chitins, chitomannans. It is further mentioned by the Applicant that the present invention is not limited to the excipients listed above. The man in the art is able to choose the best excipients suitable to a particular administration form.

In a fourth aspect, the present invention further relates to a wound-treating medical device comprising a wound treating agent or a wound treating composition as described above.

In a preferred embodiment, the medical device is in the form of a dressing, bandage, transdermic medical device, controlled drug release medical device, or a drug-eluting stent.

Suitable dressings within the meaning of the invention are, without any limitation, hydrocolloid dressings, hydrocellular dressings, alginate dressings, hydrogel dressings, chitosan based dressings, cellulose derivatives dressings and any other type of dressing dedicated to wound protection and repair.

By "transdermic medical devices" it is meant a device for slow liberation via transdermic process of a substance, such as for example adhesive patch.

By "drug-eluting stent", also called "coated" or "medicated" stent, it is meant a stent that has been coated with the active substance "protein 156A".

The invention also relates to the use of the wound-treating agent, the wound-treating composition, or of the wound-treating medical device as described above, for the treatment of acute wounds and/or chronic wounds.

The invention also relates to the use of a polypeptide having the amino acid sequence of SEQ ID NO:2, or of a polypeptide having at least 50%, preferably 70%, more preferably 90% identity with the amino acid sequence of SEQ ID NO:2, in the manufacture of a pharmaceutical composition, for the treatment of acute wounds and/or chronic wounds Basically, acute wounds may be classified into different types, according to the object that caused the wound. For example, incisions or incised wounds, lacerations, abrasions and grazes, burns, puncture wounds caused by an object puncturing the skin, such as a nail or a needle, penetration wounds caused by an object such a knife entering the body, gunshot wounds caused by a bullet or similar projectile driving into or through the body. Acute wounds may also be closed wounds, such as contusions or bruises, haematoma, crushing injuries caused by a great or extreme amount of force applied over a long period of time. Other acute wounds are due to dermatologic diseases such as psoriasis, acne and eczema.

Another type of wounds which may be treated by the invention is chronic wounds. Common chronic wounds are venous ulcers, which usually occur in the legs and mostly affect the elderly, diabetic ulcers which is another major cause of chronic wounds, pressure ulcers, which usually occur in people with conditions such as paralysis that inhibit movement of body parts that are commonly subjected to pressure such as the heels, shoulder blades and sacrum, corneal ulcers, most commonly caused by an infection with bacteria, viruses, fungi or amoebae, and digestive ulcers. Other types of chronic wounds may be due to causes such as ischemia and radiation poisoning.

The present invention will now be further described with reference to the following non-limiting examples.

EXAMPLE 1

Production of the Recombinant Protein 156A

Protein 156A is a recombinant protein corresponding to the entire protein coded by the gene 156. Protein 156A was expressed in *Escherichia coli* B121(DE3)pLys, extracted from bacterial cell with 8M urea and purified onto metal ion (Ni) chelating columns using liquid chromatography. The purity of the purified recombinant protein 156A was controlled by SDS-PAGE and shown to be over 65%. Before use, endotoxins were eliminated from the solution containing the purified protein 156A using Endo-Trap columns (Phamacia) and tested. The purified endotoxin-free recombinant protein 156A was conserved in a Tris-HCl buffer solution at pH 7.5 containing 2M urea, 150 mM NaCl and 0.1 mM $CaCl_2$.

EXAMPLE 2

Stimulation of Endothelial Cell Migration by the Protein 156A in vitro

Cell migration was tested by the wound assay described by Sato and Rifkin (J Cell Biol. 1988;107:1199) with few modifications. HUVEC grown in growth medium EGM-2MV (Cambrex) were sedded in 24-well plates at 80 000 cells per well in 500 µL of growth medium and grown to confluence at 37° C. in a humidified atmosphere containing 5% $CO_2$. Cells were scrapped with a plastic tip on one line only. After wounding, the culture medium was changed for fresh medium supplemented with 500 nM (15 µg·$mL^{-1}$) of protein 156A (Test, FIG. 1B) or not (Control, FIG. 1A). After 18 hours of culture, cells were observed and photographed under the inverted microscope (Analysis, Olympus, Rungis, France).

Figure 1A:
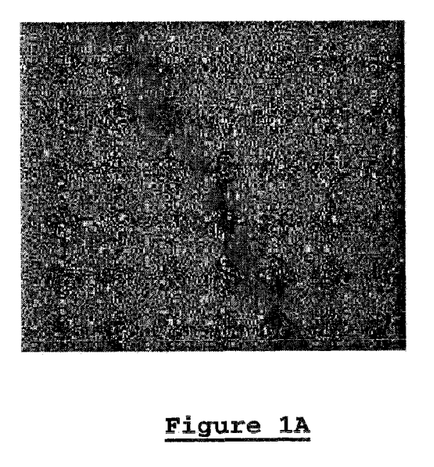
FIGS. 1A and 1B: Pictures of HUVEC endothelial cell lawn after a wound in vitro assay. After wounding, cells are incubated with VEGF and FGF2 (1A) or with VEGF, FGF2 and protein 156A (1B).

FIG. 1A shows that, 18 hours post incubation, the wound is still present under the control condition (growth medium only).

Figure 1B:
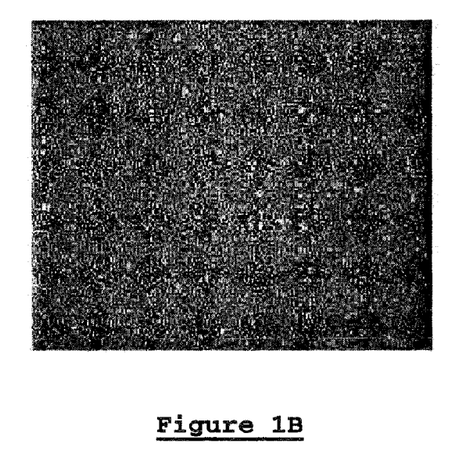

FIG. 1B shows that, 18 hours post incubation, the wound is completely healed under the Test condition (growth medium+ protein 156A).

Since migration of endothelial cells is one of the critical features of neovascularisation and wound repair, protein 156A is thus a potential therapeutic lead for wound healing.

EXAMPLE 3

Figure 2A:
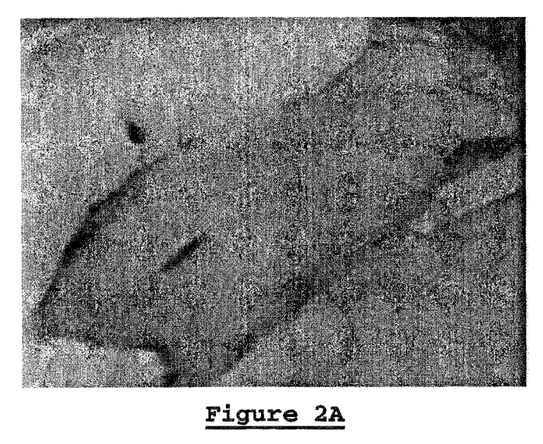
FIG. 2A: Pictures of wounds performed on Nude mice.

Pilot Experiment of the Healing Activity of Protein 156A in Swiss Nude Mice in vivo Two animals were anesthetized by IP injection of Ketamine-Xylazine (80 mg/kg-12 mg/kg; Ref. K-113, Sigma, France) and then trans-dermal injured (1 cm in length and about 1 to 2 mm in depth, see FIG. 2A) in the right flank of each mouse using 0.5/10 bladder. 200 µL of either Vehicle solution (Tris-HCl pH 7.5, 2M Urea, 150 mM NaCl, 0.1 mM $CaCl_2$) or Test solution (Vehicule+0.5 mg·$mL^{-1}$ Protein 156A) was then topically applied on the wound of animals 10 min post injury.

Figure 2B:
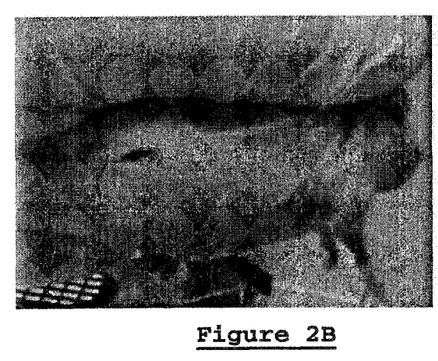
FIG. 2B: Pictures of wounds performed on Nude mice 48 hours post the topical application of vehicle solution.
Figure 2C:
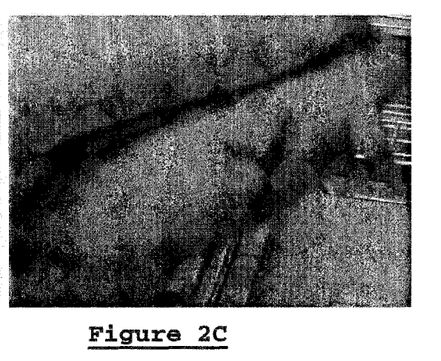
FIG. 2C: Pictures of wounds performed on Nude mice 48 hours post the topical application of protein 156A.

The examination of wound healing at 48 hours post the topical application showed that the protein 156A treated wound (see FIG. 2C) was completely healed while the vehicle treated wound (see FIG. 2B) was not yet healed and keep widely opened.

EXAMPLE 4

Test of the Healing Activity of Protein 156A in Swiss Nude Mice in vivo

Eight healthy female Swiss Nude mice were anesthetized as in example 3. Two trans-dermal wounds, each of 1 cm in length and about 1 to 2 mm in depth were realized in the right flank of each mouse using 0.5/10 bladder.

At D1, and 10 min post-injury of the animals, the 8 mice were randomized into 2 groups of 4 mice. All treatments were realized by topical application. The treatment schedule is summarized in Table 1.

TABLE 1

| Group | Animals n | Treatment | Treatment dose |
| --- | --- | --- | --- |
| 1 | 4 | Vehicle | 0 |
| 2 | 4 | Protein 156A | 0.5 mg · $mL^{-1}$ |

Mice of Group 1 were treated with 200 µL of vehicle solution (Tris-HCl pH 7.5, 2M Urea, 150 mM NaCl, 0.1 mM $CaCl_2$) topically applied on each wound, 10 minutes after wounding.

Mice of Group 2 were treated with 200 µL of Test solution (Tris-HCl pH 7.5, 2M Urea, 150 mM NaCl, 0.1 mM $CaCl_2$, 0.5 mg·$mL^{-1}$ Protein 156A) topically applied on each wound, 10 minutes after wounding.

Figure 3A:
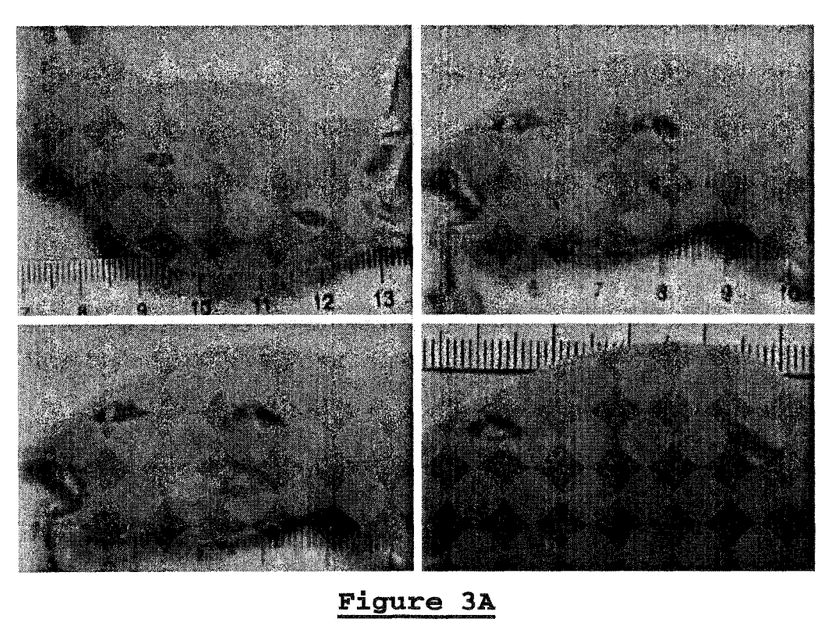
FIG. 3A: Pictures of 4 injured mice 96 hours post vehicle application.

Pictures of the wounds have been taken 96 hours after treatment with the vehicle or the test solution:

FIG. 3A: Pictures of the mice of Group 1 96 hours post vehicle application.

Figure 3B:
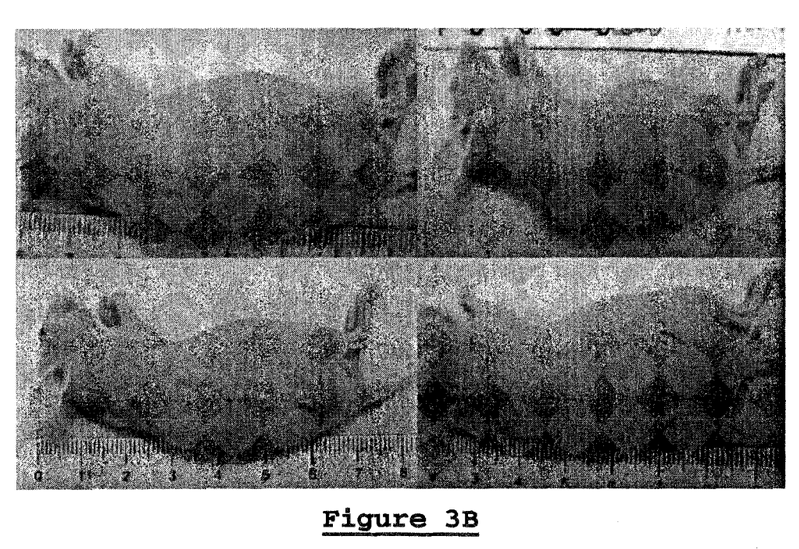
FIG. 3B: Pictures of 4 injured mice 96 hours post protein 156A application.

FIG. 3B: Pictures of the mice of Group 2 96 hours post Protein 156A application.

As illustrated by the pictures of FIG. 3, the examination of wound healing at 96 hours post the topical application showed that the Protein 156A treated wounds was completely healed (Group 2, FIG. 3B) while the vehicle treated wounds (Group 1, FIG. 3A) not yet healed and keep widely opened.

EXAMPLE 5

Test of the Healing Activity of Protein 156A in a Porcine Model in vivo

Skin Wound Healing Activity

Figure 4:
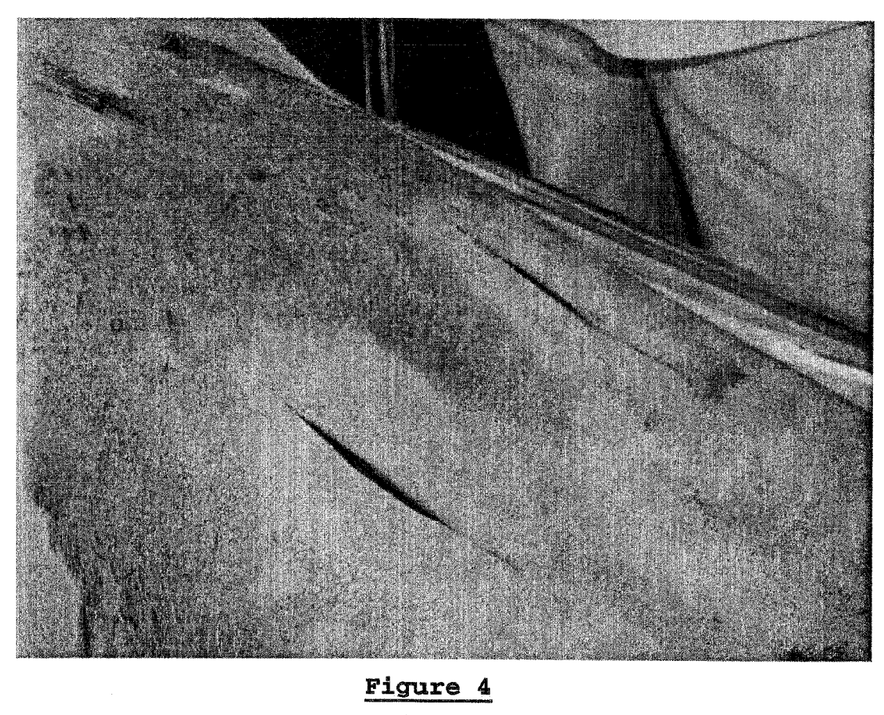
FIG. 4: Picture of two trans-dermal parallel wounds performed on the back of a farm pig.

A farm pig was anaesthetised by IM injection of Ketamine/Azaperone (10 mg/kg-2 mg/kg IM) and then two parallel longitudinal trans-dermal wounds all the way down to the hypodermis were performed (FIG. 4).

5 mL of either Vehicle solution (Tris-HCl pH 7.5, 2M Urea, 150 mM NaCl, 0.1 mM $CaCl_2$, CONTROL side "C") or Test solution (Vehicule+0.5 mg·$mL^{-1}$ Protein 156A, TEST side "T") was then topically applied on the wound of animals 10 min post injury.

Figure 5:
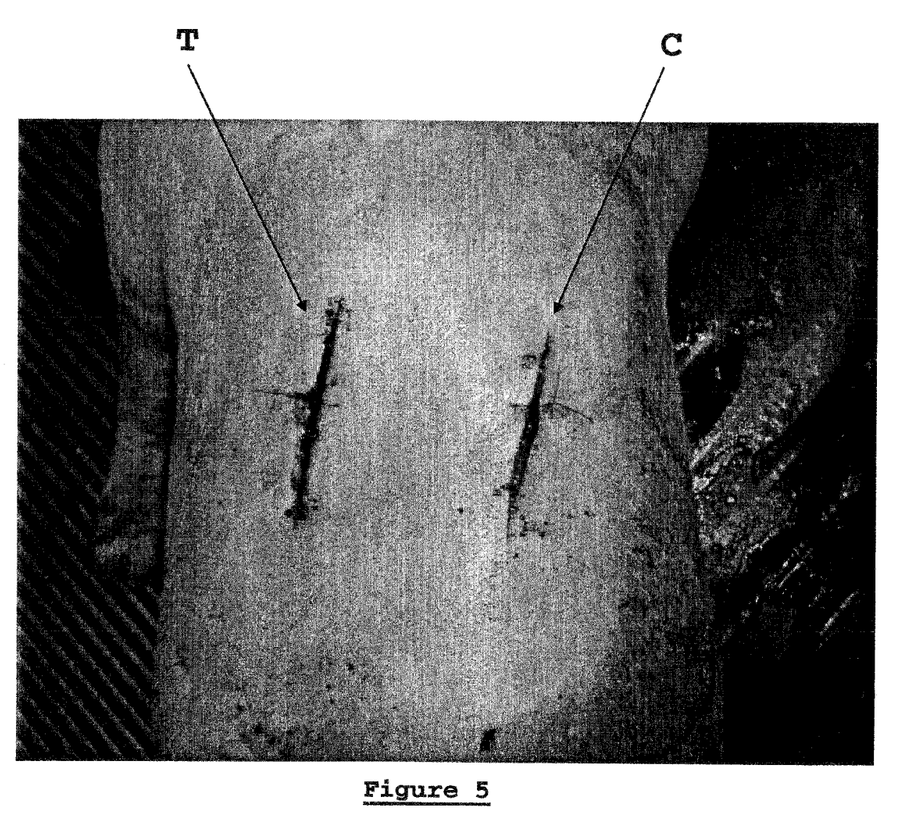
FIG. 5: Picture of the two trans-dermal parallel wounds few hours after application of vehicle solution ("C" for CONTROL) or protein 156A ("T" for TEST).
Figure 6:
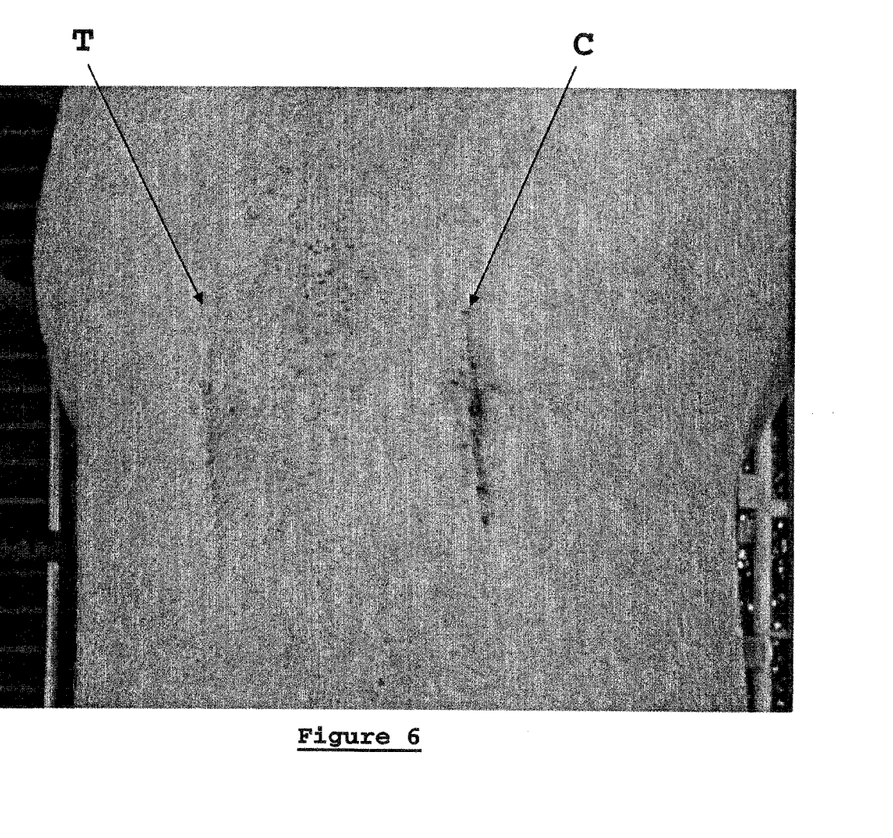
FIG. 6: Picture of the two trans-dermal parallel wounds 3 weeks after application of vehicle solution ("C" for CONTROL) or protein 156A ("T" for TEST).

Observation of both wounds showed a marked difference in the immediate postoperative period. A scab appeared in the few hours following surgery on the TEST side "T" (FIG. 5). The latter scab stayed in place for two weeks and was then rubbed of. Healing under the scab seemed normal as judged on the macroscopic appearance of the wound. After 3 weeks, the wound was smooth/even and thin (FIG. 6). The scab on the CONTROL side "C" developed only after two days. General aspects of the CONTROL wound was less even and ended up thicker and more contracted.

Cornea Wound Healing Activity

A farm pig was anaesthetised by IM injection of Ketamine/Azaperone (10 mg/kg, 2 mg/kg IM) and then superficial corneal scarifications were performed.

1 mL of either Vehicle solution (Tris-HCl pH 7.5, 2M Urea, 150 mM NaCl, 0.1 mM $CaCl_2$, CONTROL side) or Test solution (Vehicule+0.5 mg·$mL^{-1}$ Protein 156A, TEST side) was then topically applied on the scarifications 10 min post injury.

At Day 2 the animal was sacrificed and the tissues were harvested.

Oedema of the ciliary processes was observed in both the treated and non treated zones. However, while the non-ulcerated corneal epithelium was detached laterally by intense oedema in the non treated zone, this oedema was virtually absent in the treated zone.

EXAMPLE 6

Histological Analysis of Treated and Non Treated Cutaneous Wounds

A farm pig was anaesthetised by IM injection of Ketamine/Azaperone (10 mg/kg, 2 mg/kg IM) and then two parallel longitudinal trans-dermal wounds all the way down to the hypodermis were performed.

5 mL of either Vehicle solution (Tris-HCl pH 7.5, 2M Urea, 150 mM NaCl, 0.1 mM $CaCl_2$, CONTROL side) or Test solution (Vehicule+0.5 mg·$mL^{-1}$ Protein 156A, TEST side) was then topically applied on the wound of animals 10 min post injury.

At day 5 the animal was sacrificed and areas of both CONTROL wound and TEST wound were harvested Formalin-fixed, paraffin-embedded blocks were processed and serial five microns sections from the harvested areas were prepared for conventional HES staining.

Figure 7A:
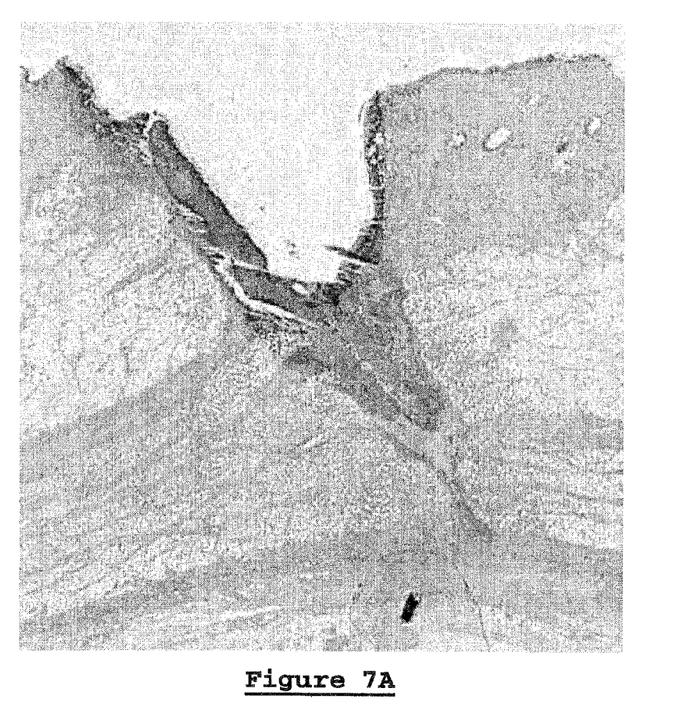
FIG. 7A: Picture of a section of a wound harvested 5 days after application of a vehicle solution.
Figure 7B:
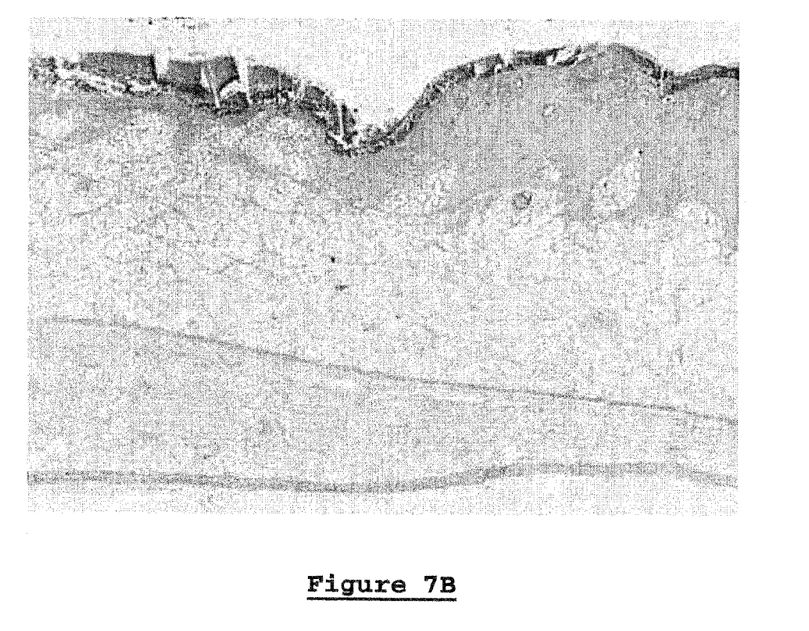
FIG. 7B: Picture of a section of a wound harvested 5 days after application of protein 156A.

In the non-treated animal (FIG. 7A), results showed that, at Day 5 post injury, the wound was still transfixing as far as the deep subdermis, while in the treated group (FIG. 7B), the approximation of the edges concern all layers of the skin (dermis and epidermis).

These different tests showed that there was a strong difference between the treated wounds and the control wounds. Healing of the Test wounds (treated with protein 156A) was all times faster, thinner and more even and complete. Final aesthetic aspect of the wound was also greater. The molecule further showed strong activity on the experimental model of corneal ulcer.

The invention claimed is:

1. A wound-treating medical device comprising a polypeptide consisting of SEQ ID NO:2, wherein said device administers a therapeutically effective amount of said polypeptide consisting of SEQ ID NO:2 to a wound causing invasion of a clot present in the wound by fibroblasts, thereby promoting wound healing.

2. The wound-treating medical device according to claim 1, being in a form selected from the group consisting of a dressing, bandage, transdermal medical device, controlled drug release medical device, and a drug-eluting stent.

3. A method for promoting wound healing, comprising administering to a subject in need thereof, a therapeutically effective amount of a polypeptide consisting of SEQ ID NO:2, wherein the polypeptide causes invasion of a clot present in the wound by fibroblasts, thereby promoting wound healing.

4. The method according to claim 3, wherein the subject has acute wounds selected from group consisting of incisions, lacerations, abrasions, puncture wounds, penetration wounds, contusions, haematoma, and crushing injuries.

5. The method according to claim 3, wherein the subject has chronic wounds caused by a condition selected from the group consisting of venous ulcers, diabetic ulcers, pressure ulcers, corneal ulcers, digestive ulcers, ischemia, radiation poisoning, and dermatologic diseases.

6. The method according to claim 3, wherein said SEQ ID NO:2 is administered by contacting a wound of the subject with a wound-treating medical device comprising said SEQ ID NO:2.

7. The method according to claim 6, wherein the medical device is in a form selected from the group consisting of a dressing, bandage, transdermal medical device, controlled drug release medical device, and a drug-eluting stent.

8. The method according to claim 3, wherein said SEQ ID NO:2 is administered by topical, systemic, oral, subcutaneous, transdermal intramuscular or intra-peritoneal administration.

9. The method according to claim 3, wherein said SEQ ID NO:2 is administered with a further active substance selected from the group consisting of an haemostatic active substance, a growth factor, an anti-infective substance, an analgesic substance, an anti-inflammatory substance, and combinations thereof.

* * * * *